(12) United States Patent
Butcher et al.

(10) Patent No.: US 6,838,291 B2
(45) Date of Patent: Jan. 4, 2005

(54) RADIOLIGAND AND BINDING ASSAY

(75) Inventors: John W. Butcher, Telford, PA (US); David A. Claremon, Maple Glen, PA (US); Thomas M. Connolly, Lansdale, PA (US); Jerzy Karczewski, Blue Bell, PA (US); Kenneth S. Koblan, Chalfont, PA (US); Matthew J. Kostura, Perkasie, PA (US); Nigel J. Liverton, Harleysville, PA (US); Dennis C. Dean, Chatham, NJ (US); David G. Melillo, Scotch Plains, NJ (US)

(73) Assignee: Merck & Co., Inc., Rahway, NJ (US)

( * ) Notice: Subject to any disclaimer, the term of this patent is extended or adjusted under 35 U.S.C. 154(b) by 110 days.

(21) Appl. No.: 09/904,045

(22) Filed: Jul. 12, 2001

(65) Prior Publication Data

US 2002/0034730 A1 Mar. 21, 2002

Related U.S. Application Data

(60) Provisional application No. 60/218,397, filed on Jul. 14, 2000.

(51) Int. Cl.$^7$ .................... G01N 33/534; G01N 33/567
(52) U.S. Cl. .................... 436/504; 435/7.21; 435/40.5; 436/166; 436/172
(58) Field of Search .............. 435/7.21, 40.5; 436/504, 166, 172, 804, 545, 519, 811

(56) References Cited

U.S. PATENT DOCUMENTS 5,633,247 A    5/1997    Baldwin et al.

FOREIGN PATENT DOCUMENTS

WO    WO 95/23146    8/1995

OTHER PUBLICATIONS

P. Spector et al, Circulation Research, Mar. 1996, 78(3), pp. 499–503. Antiarrythmic Drugs Block HERG, a Human Cardiac Delayed Rectifier K+ Channel Open–Channel Block by Methanesulfonanilides.*

C. C. Chadwick et al, Circulation Research, 72, 707–714 (1993).*

C. Fiset et al, J. Mol. Cell Cardiol., 28, 1085–1096 (1996).*

R.Geonzon et al, J. Mol. Cell Cardiol., 30, 1691–1701 (1998).*

H. J. Duff et al, Circulation Research, 77, 718–725 (1995).*

Kale, T.A., et al., Journal of the American Chemical Society, vol. 123(19), pp. 4373–4381, 2001.

Dean, D.C., et al., Synthesis and Applications of Isotopically Labelled Compounds, Paper 9, pp. 71–74, 1997.

Dean, D.C., et al., Synthesis and Applications of Isotopically Labelled Compounds, vol. 7, pp. 408–411, 2001.

Dean, D.C., et al., Synthesis and Applications of Isotopically Labelled Compounds, Paper 140, pp. 795–801, 1994.

Dean, D.C., et al., Journal of Medicinal Chemistry, vol. 39(9), pp. 1767–1770, 1996.

Vandenberg, J.I., et al., Trends in Pharmacological Sciences, vol. 22(5), pp. 240–246, 2001.

* cited by examiner

*Primary Examiner*—Mary E. Ceperley
(74) *Attorney, Agent, or Firm*—Richard S. Parr; Valerie J. Camara; Mark R. Daniel

(57) ABSTRACT

The present invention is directed to the radioligand compound, [$^{35}$S]-radiolabeled (+)-N-[1'-(6-cyano-1,2,3,4-tetrahydro-2(R)-naphthalenyl)-3,4-dihydro-4(R)-hydoxyspiro[2H-1-benzopyran-2,4'-piperidin]-6-yl] methanesulfonamide. Also within the scope of this invention is a method for identifying compounds that bind to the $I_{Kr}$ channel, and may have antiarrhythmic activity.

16 Claims, No Drawings

RADIOLIGAND AND BINDING ASSAY

This application claims benefit of 60/218,397 filed Jul. 14, 2000.

BACKGROUND OF THE INVENTION

The present invention provides for a radioligand compound that is a useful agent to screen for potential Class III antiarrhythmic compounds and method of screening for this $I_{Kr}$ activity using this radioligand compound. In the past, a similar binding assay was conducted using a [$^3$H]-radioligand capable of binding to ether-a-go-go-related gene (ERG) in guinea pig myocytes or patch clamping on intact cells were carried out. See Geonzon, R. et al. J. Mol. Cell Cardiol. 30, p.1691–1701 (1998); Chadwick, C. C. et al. Circulation Research 72, p.707–714 (1993); Duff, H. J. et al. Circulation Research 77, p.718–725 (1995); and Fiset, C. et al. J. Mol. Cell Cardiol. 28, p.185–1096 (1996).

The present invention offers several advantages over the previous methods. Use of a [$^{35}$S]-labeled radioligand offers the advantage that [$^{35}$S] is a higher energy and specific activity radioisotope than [$^3$H], allowing for scientists to refine the assay conditions with the use of less radioligand and human ERG (also referred to as hERG) channel, as well as the ability to set up a more sensitive assay. The current binding assay has also been developed using membranes from cells expressing hERG, rather than ERG in intact animal cells, as the source of the ion channel. Thus, the use of human ERG in the present assay will provide investigators with a more relevant binding assay over the animal ERG.

Additionally, membranes are a more convenient source of the ion channel compared to intact cells. A larger throughput is possible as a large amount of the membrane can be made in advance, stored frozen and thawed on the day of the assay. Also, a membrane source of ion channel has both its extracellular and intracellular sites exposed and is not dependent on changes in the physiology of an intact cell for all potential binding sites to be exposed. A final advantage of the [$^{35}$S]-based binding assay is that it can be carried out with much higher throughput compared to a whole cell patch clamp assay. Thus, the current invention is more suited to broad-based screening. This assay is used as a counterscreen in research programs where long QT activity is not desirable.

U.S. Pat. No. 5,633,247 discloses and claims the unlabelled compound (also referred to as the cold ligand), N-[1'-(6-cyano-1,2,3,4-tetrahydro-2(R)-naphthalenyl)-3,4-dihydro-4(R)-hydoxyspiro[2H-1-benzopyran-2,4'-piperidin]-6-yl]-methanesulfonamide.

SUMMARY OF THE INVENTION

This invention relates to a radioligand compound, [$^{35}$S]-radiolabeled (+)-N-[1'-(6-cyano-1,2,3,4-tetrahydro-2(R)-naphthalenyl)-3,4-dihydro-4(R)-hydoxyspiro[2H-1-benzopyran-2,4'-piperidin]-6-yl]methanesulfonamide (Formula I) or pharmaceutically acceptable salts, hydrates or solvates thereof. Also within the scope of this invention is a method for identifying compounds that bind to the $I_{Kr}$ channel.

DETAILED DESCRIPTION OF THE INVENTION

A radioligand compound of Formula I

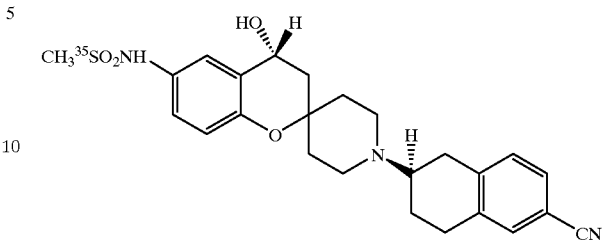

or pharmaceutically acceptable salts, hydrates, or solvates thereof. The radioligand compound of Formula I is also referred to as [$^{35}$S]-radiolabeled (+)-N-[1'-(6-cyano-1,2,3,4-tetrahydro-2(R)-naphthalenyl)-3,4-dihydro-4(R)-hydoxyspiro[2H-1-benzopyran-2,4'-piperidin]-6-yl]-methanesulfonamide. The compound of Formula II is the unlabeled compound, (+)-N-[1'-(6-cyano-1,2,3,4-tetrahydro-2(R)-naphthalenyl)-3,4-dihydro-4(R)-hydoxyspiro[2H-1-benzopyran-2,4'-piperidin]-6-yl] methanesulfonamide.

An embodiment of the invention includes the radioligand compound of Formula I which possesses a specific activity of greater than about 500 Ci/mmol., and preferably in the range of about 900 Ci/mmol. to about 1498 Ci/mmol.

A method of characterizing an ion channel as an $I_{Kr}$ channel comprising contacting the ion channel with the radioligand compound, [$^{35}$S]-radiolabeled (+)-N-[1'-(6-cyano-1,2,3,4-tetrahydro-2(R)-naphthalenyl)-3,4-dihydro-4(R)-hydoxyspiro[2H-1-benzopyran-2,4'-piperidin]-6-yl] methanesulfonamide, and determining if the radioligand compound binds to the ion channel.

A method for characterizing the activity of a compound as an $I_{Kr}$ channel blocker comprising contacting the test compound with a membrane containing the $I_{Kr}$ channel in the presence of the radioligand compound, [$^{35}$S]-radiolabeled (+)-N-[1'-(6-cyano-1,2,3,4-tetrahydro-2(R)-naphthalenyl)-3,4-dihydro-4(R)-hydoxyspiro[2H-1-benzopyran-2,4'-piperidin]-6-yl]methanesulfonamide, and monitoring whether the test compound influences the binding of the radioligand compound to the membrane containing the $I_{Kr}$ channel. The membrane containing the $I_{Kr}$ channel is derived from an appropriate cell line capable of being stably transfected with the ERG gene and expressing the $I_{Kr}$ channel protein, representative examples of the same are the HEK 293 cells (ATCC No. CRL-1573, American Type Culture Collection 10801 University Boulevard, Manassas, Va. 20110) or CHO cells that have been stably transfected with the human, canine or primate ERG gene and are capable of expressing the $I_{Kr}$ channel protein. The human ERG gene is disclosed in T. Itoh, et al. Human Genetics 102(4), pp. 435–439 (1998) and M. D. Adams, et al. Nature 377:3–174 (1995). The radioligand compound useful in this method possesses a specific activity of greater than 500 Ci/mmol., and preferably in the range of about 900 Ci/mmol. to about 1498 Ci/mmol.

A method for assessing the binding of a test compound to a membrane containing the $I_{Kr}$ channel using a radioligand of Formula I, [$^{35}$S]-radiolabeled (+)-N-[1'-(6-cyano-1,2,3,4-tetrahydro-2(R)-naphthalenyl)-3,4-dihydro-4(R)- hydoxyspiro[2H-1-benzopyran-2,4'-piperidin]-6-yl]methanesulfonamide, comprising the steps of:

1) preparing solutions of the test compound at 5 or more different concentrations, a solution of control vehicle and a solution of (+)-N-[1'-(6-cyano-1,2,3,4-tetrahydro-2(R)-naphthalenyl)-3,4-dihydro-4(R)-hydoxyspiro[2H-1-benzopyran-2,4'-piperidin]-6-yl]-methanesulfonamide (compound of Formula II) in a solvent;
2) mixing the radioligand compound of Formula I with the membrane containing the $I_{Kr}$ channel diluted with an assay buffer to form a membrane/radioligand mixture of known concentration;
3) incubating a quantity of known concentration of the membrane/radioligand mixture with the solution of test compound, control vehicle or compound of Formula II, as recited in Step 1, for a set time period at a temperature range of between about 4° C. and about 37° C. to give a mixture of membrane bound with the radioligand and the test compound, the control vehicle or the compound of Formula II, where the final concentration of the membrane containing the $I_{Kr}$ channel is predetermined;
4) isolating from the incubated mixture the membrane bound with the radioligand and the test compound, the control vehicle or the compound of Formula II;
5) measuring the radioactivity of the isolated membrane bound with the radioligand and the test compound, the control vehicle or the compound of Formula II;
6) repeating steps 3 through 5 with the test compound at each concentration, the solution of control vehicle and the solution of the compound of Formula II, as recited in Step 1; and
7) calculating the $IC_{50}$ corresponding to the measured radioactivity of: 1) the membrane bound with the radioligand and each concentration of the test compound, 2) the membrane bound with the radioligand and with the control vehicle, and 3) the membrane bound with the radioligand and the compound of Formula II.

The potency of compound interaction with the $I_{Kr}$ channel or $IC_{50}$, is determined by comparing the [$^{35}$S]-radioligand counts bound to the membranes in the presence of a solvent vehicle (100% control), in the presence of 1 μM Formula II (final non-specific binding) and at each of seven different concentrations of the test compound. The number of different concentrations tested can be more or less than seven. A 100 μM solution of the test compound in a solvent, such as dimethylsulfoxide (DMSO), methanol, water or buffer, is prepared and seven concentrations of the test compound are prepared by through either log (10-fold) dilutions, 5-fold dilutions or 3-fold dilutions of the stock 100 μM solution of test compound. The percent control value is determined for each condition and a non-linear 4 parameter regression plot is made and the inflection point or $IC_{50}$, of this plot is determined. This value is reported as a measure of the compound's affinity of interaction with the ERG channel. When the data do not adequately fit the 4 parameter equation either the maximum or minimum binding, or both, are fixed and either a 3 or 2 parameter fit, respectively, are used to generate the inflection point.

The membrane-bound radioligand is monitored after isolation by either filtration from the free radioligand using for example the Unifilter (Packard), or by using alternate techniques that include the Scintillation Proximity Assay (SPA) beads (Amersham Pharmacia Biotech) or the Flashplates (New England Nuclear Life Sciences). Use of the latter two techniques requires the incubation of the membranes, radioligand and compound with either the SPA bead in a standard assay plate or in a Flashplate.

A method for assessing the binding of a test compound to a membrane containing the $I_{Kr}$ channel using a radioligand of Formula I, [$^{35}$S]-radiolabeled (+)-N-[1'-(6-cyano-1,2,3,4-tetrahydro-2(R)-naphthalenyl)-3,4-dihydro-4(R)-hydoxyspiro[2H-1-benzopyran-2,4'-piperidin]-6-yl]-methanesulfonamide, comprising the steps of:

1) preparing assay wells with 4 μl of the test compound in dimethylsulfoxide (DMSO) diluted 100× with assay buffer at 5 or more different concentrations, a control vehicle of DMSO and a DMSO solution of (+)-N-[1'-(6-cyano-1,2,3,4-tetrahydro-2(R)-naphthalenyl)-3,4-dihydro-4(R)-hydoxyspiro[2H-1-benzopyran-2,4'-piperidin]-6-yl]-methanesulfonamide (compound of Formula II);
2) adding the radioligand compound of Formula I at 50 pM to the membrane containing the $I_{Kr}$ channel diluted with assay buffer to form a membrane/radioligand mixture;
3) incubating each assay well with 400 μl of the 50 pM membrane/radioligand mixture for about 75 minutes to about 90 minutes at room temperature (25° C.) to give assay wells containing the membrane bound with the radioligand and the test compound at each concentration, the DMSO control vehicle or the compound of Formula II where the final concentration of the membrane containing the $I_{Kr}$ channel is 11 μg/ml;
4) filtering the incubated assay wells through 0.1% BSA presoaked filters to isolate on the filters the membrane bound with the radioligand and the test compound at each concentration, the DMSO control vehicle or the compound of Formula II;
5) washing each of the filters containing the membrane bound with the radioligand and the test compound at each concentration, the DMSO control vehicle or the compound of Formula II about 5 times with 500 μl of ice cold wash buffer;
6) drying the washed-filters containing the membrane bound with the radioligand and the test compound at each concentration, the DMSO control vehicle or the compound of Formula II at room temperature in a fume hood;
7) adding 50 μl Microscint-20 microscintillate to the dried-filters containing the membrane bound with the radioligand and the test compound at each concentration, the DMSO control vehicle or the compound of Formula II;
8) measuring the microscintillation count of the microscintillation-treated filters containing the membrane bound with the radioligand and the test compound at each concentration, the DMSO control vehicle or the compound of Formula II for one minute; and
9) calculating the $IC_{50}$ corresponding to the measured microscintillation count of: 1) the microscintillation-treated filters containing the membrane bound with the radioligand and each concentration of the test compound, 2) the microscintillation-treated filters containing the membrane bound with the radioligand and with the control vehicle, and 3) the microscintillation-treated filters containing the membrane bound with the radioligand and the compound of Formula II.

The method as recited above, wherein the membrane containing the $I_{Kr}$ channel is derived from a cell line transfected with the ERG gene, wherein the cell line is HEK 293 cells or CHO cells, and preferably HEK 293 cells and wherein the ERG gene is human, canine or primate and preferably human or canine.

The method as recited above, wherein the solutions of the test compound are prepared in Step 1 at 7 different concentrations (dilutions).

The method as recited above, wherein the radioligand compound of Formula I possesses a specific activity of in the range of greater than 500 and preferably in the range of about 900 Ci/mmol. to about 1498 Ci/mmol. The method as recited above, wherein the membrane bound with the radioligand and the test compound at each concentration, the DMSO control vehicle or the compound of Formula II is filtered in Step 4 with Unifilters (Parkard).

An embodiment of the invention is the process for the preparation of

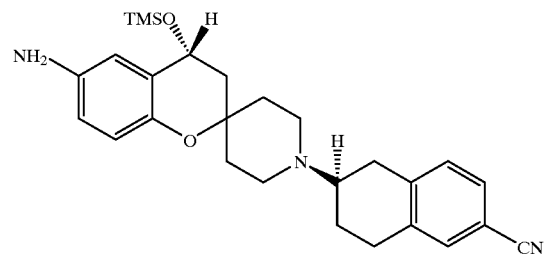

a key intermediate in the preparation of the radioligand compound of Formula I, which comprises the steps of (1) reacting the alcohol with 2,6-lutidine and t-butyldimethylsilyl triflate

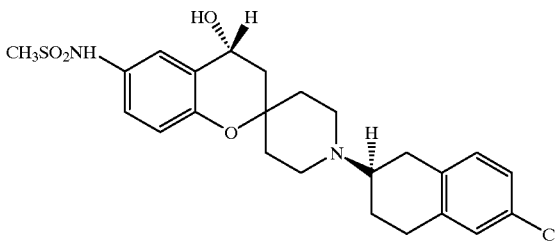

to give a t-butyldimethylsilyl-protected hydroxyl compound

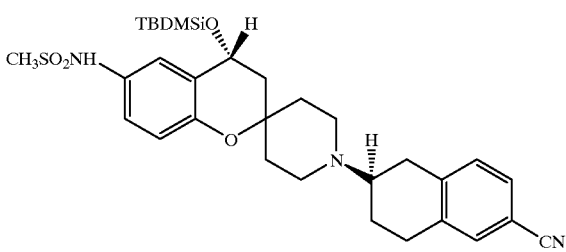

(2) alkylating the t-butyldimethylsilyl-protected hydroxyl compound by treating with sodium hydride, and then treating with 2-trimethylsilylethanesulfonylchloride to give the disubstituted sulfonamide compound

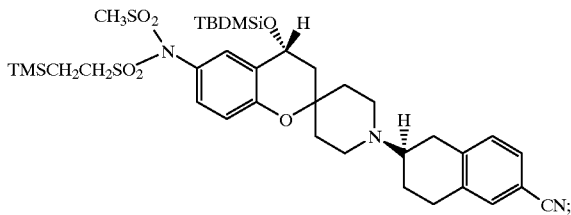

(3) treating the disulfonamide with an $C_1$–$C_8$-alkanethiolate to give a mixture of the following sulfonamides;

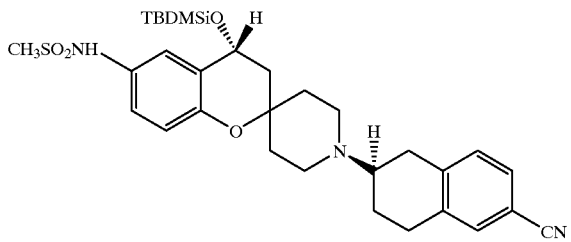

and

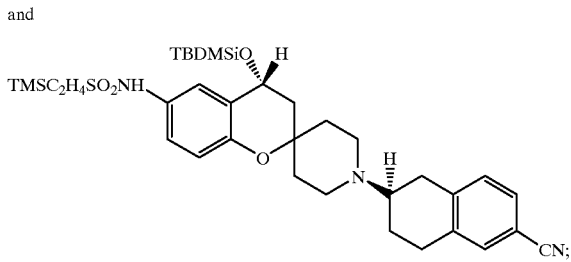

(4) separating the sulfonamide mixture using chromatography to isolate the non-polar sulfonamide eluting with a non-polar solvent system

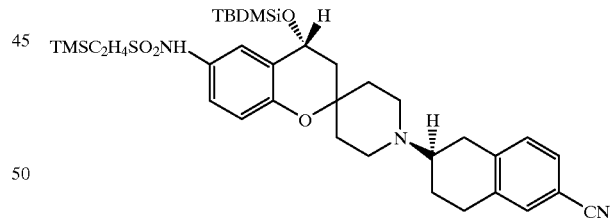

and then eluting off the polar isomer using a polar solvent system

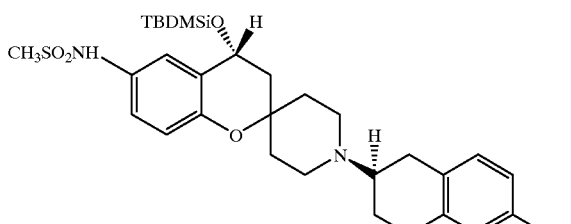

(5) desulfonating the non-polar isomer

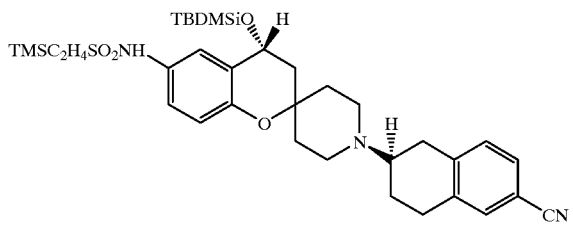

using a fluoride compound in an organic solvent and heating for about 24 hours to about 48 hours to give the free alcohol-amine

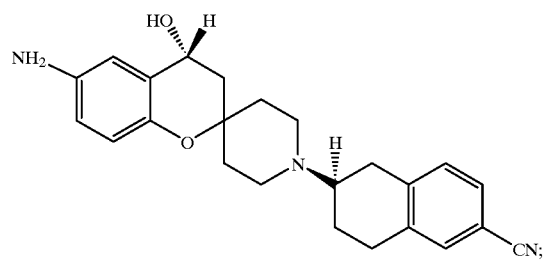

(6) reacting the free alcohol-amine with trimethylsilylimidazole in an organic solvent

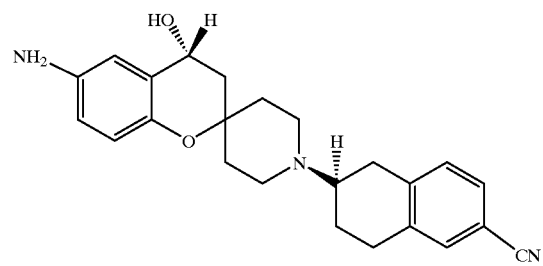

to give the desired trimethylsilyloxy compound.

The starting material (also referred to as the compound of Formula II) for the process as recited above is described in U.S. Pat. Nos. 5,633,247, 5,206,240, 5,484,923 and 5,464,762. Additionally, an asymmetric synthesis of the tetrahydronapthalene intermediate in the synthesis of this starting material is described in British Publication No. 2,290,790 published on Jan. 10, 1996. The process as recited above, wherein the alkylation in step 2 is stirred at room temperature for up to 24 hours, and preferably for 18 hours. The process as recited above, wherein the $C_1$–$C_8$-alkanethiolate used in step 3 is a branched or straight chain alkanethiolate, such as sodium or potassium hexanethiolate, sodium or potassium butanethiolate, sodium or potassium 2-methylpentanethiolate, sodium or potassium 2-methylpropanethiolate, sodium or potassium methanethiolate, sodium or potassium ethanethiolate and preferably sodium 2-methylpropanethiolate. The process as recited above, wherein the desulfonylation reaction in step 3 is run for less than 24 hours, preferably for about 30 minutes to one hour. The process as recited above, wherein the separation of the sulfonamide mixture in step 4 is run using flash chromatography with a solvent system of ethyl acetate and hexane to ethyl acetate and methanol, and preferably with a non-polar solvent system of 1:1 ethyl acetate: hexane and a polar solvent system of 99:1 ethyl acetate: methanol. The process as recited above, wherein the fluoride compound used in the desulfonylation of step 5 is selected from: cesium fluoride (CsF), and tetrabutylammonium fluoride, and preferably CsF. The process as recited above, wherein the organic solvent used in the desulfonylation of step 5 is selected from: dimethylformamide (DMF), dimethylsulfoxide, and N-methylpyrrolidinone, and is preferably DMF. The process as recited above, wherein the organic solvent in step 6 is acetonitrile, tetrahydrofuran, or ether, and preferably is acetonitrile.

An embodiment of the invention is a process for the preparation of a radioligand compound of Formula I

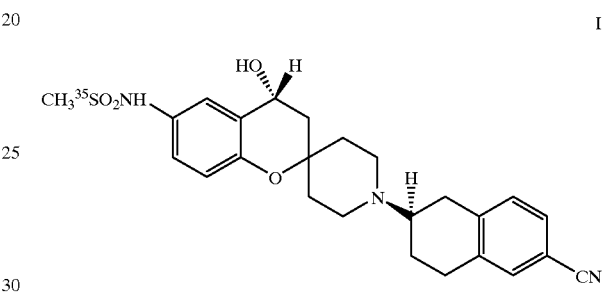

I comprising the steps of:

(a) reacting the amine

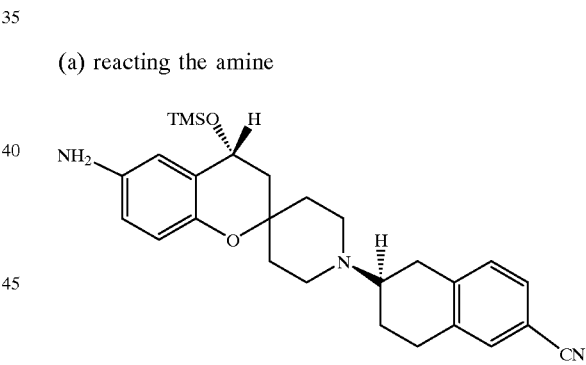

with [$^{35}$S]-methanesulfonyl chloride in the presence of an organic base to form the silyl-protected [$^{35}$S]-methanesulfonamide; and (b) removing the silyl-protecting group of the silyl-protected [$^{35}$S]-methanesulfonamide with trifluoroacetic acid to give the radioligand compound of Formula I.

The process, wherein an organic base such as triethylamine, trimethylamine, and diisopropylethylamine is used, preferably triethylamine. The process is preferably run at room temperature for about 2 hours under anhydrous conditions.

Also within the scope of the invention is the key intermediate in the synthesis of the radioligand compound of Formula I, which is the amine compound,

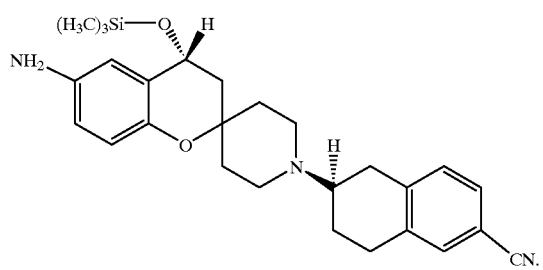

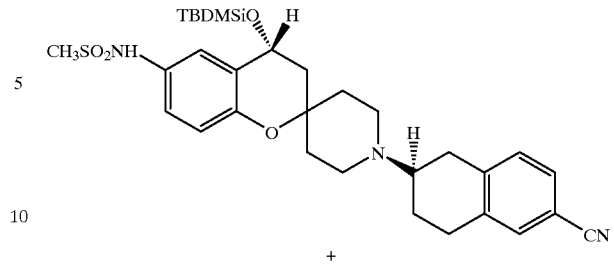

+

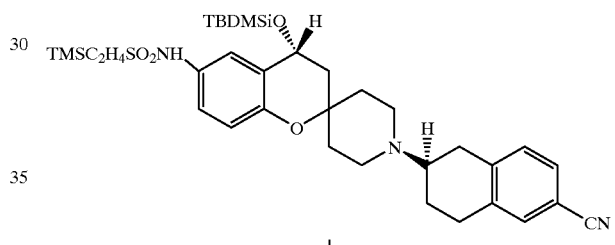

SCHEME 2

The radioligand compound [³⁵S]-radiolabeled (+)-N-[1'-(6-cyano-1,2,3,4-tetrahydro-2(R)-naphthalenyl)-3,4-dihydro-4(R)-hydoxyspiro[2H-1-benzopyran-2,4'-piperidin]-6-yl]methanesulfonamide is prepared utilizing the following synthetic route. Schemes 1 and 2 describe the steps for preparing N-[1'-(6-cyano-1,2,3,4-tetrahydro-2(R)-naphthalenyl)-3,4-dihydro-4(R)-trimethylsilyloxyspiro[2H-1-benzopyran-2,4'-piperidin]-6-yl]amine from N-[1'-(6-cyano-1,2,3,4-tetrahydro-2(R)-naphthalenyl)-3,4-dihydro-4(R)-hydroxyspiro[2H-1-benzopyran-2,4'-piperidin]-6-yl]methanesulfonamide. Scheme 3 describes preparation of the radiolabeled methanesulfonyl chloride, using sodium [³⁵S]-sulfite to prepare sodium [³⁵S]-methanesulfonate which is then converted to the sulfonyl chloride, and the sulfonylation of the amine with the radiolabeled methanesulfonyl chloride, followed by the removal of the trimethylsilyl protecting group.

SCHEME 1

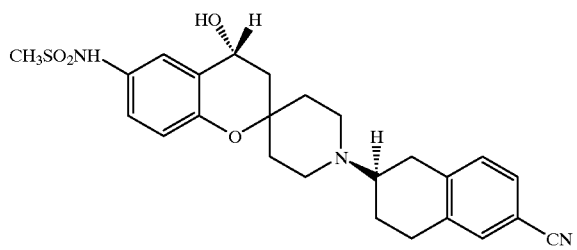

| TBDMSi-triflate
2,6-lutidine, CH₂Cl₂
0° C., 3h.

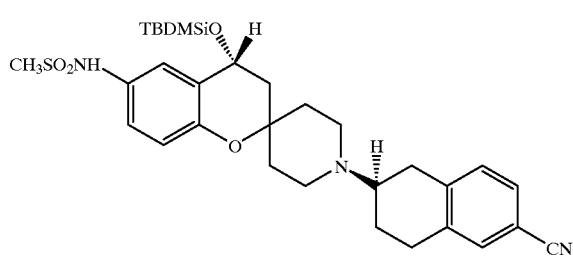

1) NaH, THF, -20° C., 30 min., Ar(g)
2) TMSC₂H₂SO₂Cl, 18h
3) CH₃CH(CH₃)CH₂SNa, 30 min.

| CsF, DMF, Ar(g)
95° C., 30h

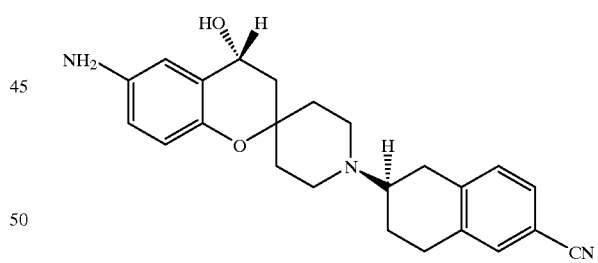

| TMS-imidazole
ACN, Ar(g),
60° C., 1.5h

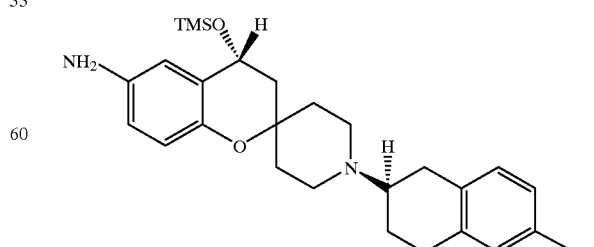

SCHEME 3

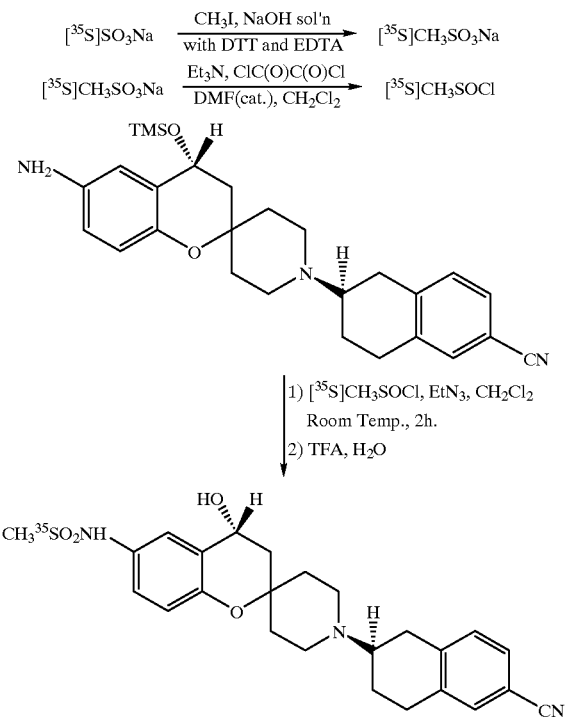

1) [³⁵S]CH₃SOCl, EtN₃, CH₂Cl₂
   Room Temp., 2h.
2) TFA, H₂O

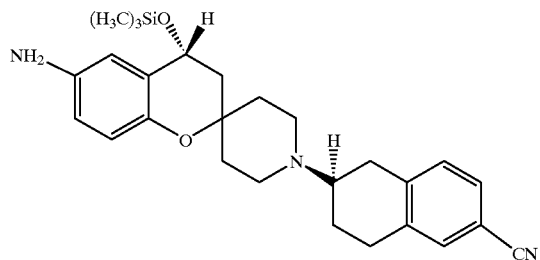

The following examples illustrate this invention, and as such are not to be considered as limiting the invention set forth in the claims appended hereto.

EXAMPLE 1

N-[1'-(6-cyano-1,2,3,4-tetrahydro-2(R)-naphthalenyl)-3,4-dihydro-4(R)-trimethylsilyloxyspiro[2H-1-benzopyran-2,4'-piperidin]-6-yl]amine Step A: N-[1'-(6-cyano-1,2,3,4-tetrahydro-2(R)-naphthalenyl)-3,4-dihydro-4(R)-t-butyldimethylsilyloxyspiro[2H-1-benzopyran-2,4'-piperidin]-6-yl]methanesulfonamide To a −20° C. solution of N-[1'-(6-cyano-1,2,3,4-tetrahydro-2(R)-naphthalenyl)-3,4-dihydro-4(R)-hydroxyspiro[2H-1-benzopyran-2,4'-piperidin]-6-yl] methanesulfonamide (5.0 gm, 10.7 mmol) in dichloromethane (50 mL) under argon was added 2,6-lutidine (3.74 mL, 32.1 mmole) followed by t-butyldimethylsilyl triflate (6.46 mL, 26.8 mmole). The reaction mixture was allowed to stir at 0° C. for 3 hrs. until complete. The reaction was concentrated in vacuo, diluted with methanol and 1N sodium hydroxide slowly added (110 mL). The mixture was stirred for 30 min. extracted with ethyl acetate (2×200 mL), dried over sodium sulfate and concentrated in vacuo to an oil (9 gm). Purification by flash chromatography using 95/5 dichloromethane/acetone followed by 90/10/3 dichloromethane/acetone/methanol gave upon concentration N-[1'-(6-cyano-1,2,3,4-tetrahydro-2(R)-naphthalenyl)-3,4-dihydro-4(R)-t-butyldimethylsilylhydroxyspiro[2H-1-benzopyran-2,4'-piperidin]-6-yl]methanesulfonamide (5.5 gm, 88%) as a white solid. MS m/z 582 (M⁺).

Step B: Preparation of N-[1'-(6-cyano-1,2,3,4-tetrahydro-2(R)-naphthalenyl)-3,4-dihydro-4(R)-t-butyldimethylsilyloxyspiro[2H-1-benzopyran-2,4'-piperidin]-6-yl]trimethylsilylethanesulfonamide To a solution of N-[1'-(6-cyano-1,2,3,4-tetrahydro-2(R)-naphthalenyl)-3,4-dihydro-4(R)-t-butyl-dimethylsilyloxyspiro[2H-1-benzopyran-2,4'-piperidin]-6-yl]methanesulfonamide (2.5 gm, 4.30 mmol) in tetrahydrofuran under argon was added sodium hydride (60% disp., 0.50 gm, 13.0 mmole). The mixture was allowed to stir for 30 min. cooled to −20° C. and trimethylsilylethanesulfonyl chloride (2.5 mL, 12.4 mmole) added. The reaction was allowed to stir for 18 hrs., after which sodium 2-methylpropanethiolate (5.0 gm, 44.0 mmole) was added in one portion. The reaction was allowed to stir for 30 min. diluted with water (200 mL) and extracted with ethyl acetate (400 mL). The organic extract was washed with brine, dried over sodium sulfate, concentrated in vacuo to an oil and purified by flash chromatography using 1/1 ethyl acetate/hexane to give N-[1'-(6-cyano-1,2,3,4-tetrahydro-2(R)-naphthalenyl)-3,4-dihydro-4(R)-t-butyldimethylsilyloxyspiro[2H-1-benzopyran-2,4'-piperidin]-6-yl] trimethylsilylethanesulfonamide (1.43 gm, 50%), followed by 99/1 ethyl acetate/methanol to give N-[1'-(6-cyano-1,2,3,4-tetrahydro-2(R)-naphthalenyl)-3,4-dihydro-4(R)-t-butyl-dimethylsilyloxyspiro[2H-1-benzopyran-2,4'-piperidin]-6-yl]methanesulfonamide (1.1 gm, 44%). MS m/z 668 (M⁺).

Step C: Preparation of N-[1'-(6-cyano-1,2,3,4-tetrahydro-2(R)-naphthalenyl)-3,4-dihydro-4(R)-hydroxyspiro[2H-1-benzopyran-2,4'-piperidin]-6-yl]-amine To a mixture of N-[1'-(6-cyano-1,2,3,4-tetrahydro-2(R)-naphthalenyl)-3,4-dihydro-4(R)-t-butyldimethylsilyloxyspiro[2H-1-benzopyran-2,4'-piperidin]-6-yl]trimethylsilylethanesulfonamide (0.50 gm, 0.75 mmole) in dimethylformamide (5 mL) under argon was added cesium fluoride (0.34 gm, 2.25 mmole) and the mixture heated to 95° C. for 30 hrs. The reaction was cooled diluted with 10% aqueous sodium bicarbonate (50 mL) and extracted with ethyl acetate (2×50 mL). The organic extracts were dried over sodium sulfate concentrated in vacuo to an oil and purified by flash chromatography using 90/10 dichloromethane/methanol to give N-[1'-(6-cyano-1,2,3,4-tetrahydro-2(R)-naphthalenyl)-3,4-dihydro-4(R)-hydroxyspiro-[2H-1-benzopyran-2,4'-piperidin]-6-yl]amine, (0.218 gm, 80%) as a foam. MS m/z 390 (M⁺), ¹H NMR (CDCL₃) δ 1.4–2.2 (9 H, m), 2.6–3.2 (9 H, m), 3.4 (2 H, br s), 4.82 (1 H, br t), 6.60 (1 H, dd, J=9.3 and 2.8 Hz), 6.71(1 H, d, J=9.3 Hz), 6.81 (1 H, d, J=2.8 Hz), 7.18 (1 H, d, J=9.3 Hz), 7.37 (2 H, m).

Step D: Preparation of N-[1'-(6-cyano-1,2,3,4-tetrahydro-2(R)-naphthalenyl)-3,4-dihydro-4(R)-trimethylsilyloxyspiro[2H-1-benzopyran-2,4'-piperidin]-6-yl]amine To a solution of N-[1'-(6-cyano-1,2,3,4-tetrahydro-2(R)-naphthalenyl)-3,4-dihydro-4(R)-hydroxyspiro[2H-1-benzopyran-2,4'-piperidin]-6-yl]amine (50 mg, 0.128 mmole) in acetonitrile under argon was added trimethylsilylimidazole (0.36 gm, 2.5 mmole) and the reaction warmed to 60 C. for 1.5 hrs. The reaction was concentrated in vacuo and purified by flash chromatography using 95/5/0.1 dichloromethane/methanol/triethylamine to give N-[1'-(6-cyano-1,2,3,4-tetrahydro-2(R)-naphthalenyl)-3,4-dihydro-4(R)-trimethylsilyloxyspiro[2H-1-benzopyran-2,4'-piperidin]-6-yl]amine as a foam (58 mg, 98%). MS m/z 462 (M$^+$), $^1$H NMR (CDCL$_3$) δ 0.09 (9 H, s), 1.4–2.1 (8 H, m), 2.4–2.9 (9 H, m), 3.2 (2 H, br, s), 4.65 (1 H, t), 6.41(1 H, dd, J=9.2 and 3.3 Hz), 6.49 (1 H, d, J=3.3 Hz), 6.52 (1 H, d, J=9.2 Hz), 7.03 (1 H, d, J=9.2 Hz), 7.22 (2 H, m).

EXAMPLE 2

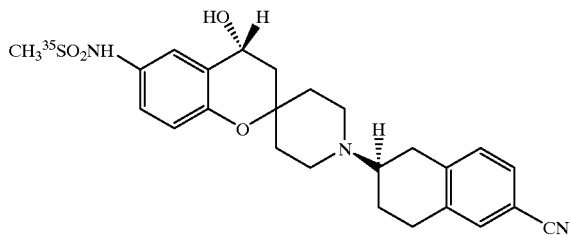

[$^{35}$S]-N-[1'-(6-cyano-1,2,3,4-tetrahydro-2(R)-naphthalenyl)-3,4-dihydro-4(R)-hydroxyspiro[2H-1-benzopyran-2,4'-piperidin]-6-yl]methanesulfonamide Step A: Sodium [$^{35}$S]-methanesulfonate To a solution of sodium [$^{35}$S]sulfite (1 Ci/mmol, 215 μCi in 100 μL of 0.1N NaOH solution with 10 mM DTT and 1 mM EDTA) (which may be obtained by reduction of [$^{35}$S] sulfuric acid on a copper surface with trapping of the generated [$^{35}$S]sulfur dioxide in sodium hydroxide solution) was added 25 μL of methyl iodide and the reaction was stirred at room temperature for 20 min. Analysis of radioactivity by HPLC (Astec cyclobond I column, gradient of 10 mM nitric acid solution to 180 mM nitric acid solution over 20 min, 1 mL/min) indicated complete conversion to [$^{35}$S]-methanesulfonic acid. The solution was concentrated under nitrogen to near dryness, 500 μL of DI water was added, and the solution was degassed with nitrogen. The resulting solution of sodium [$^{35}$S]-methanesulfonate (177 μCi) was stored at 0° C.

Step B: [$^{35}$S]-Methanesulfonyl Chloride

A solution of [$^{35}$S]-methanesulfonic acid (3.37 mCi in 2.08 g of 0.1 N sodium hydroxide, specific activity=1342 Ci/mmol, approx 90% RCP, obtained from New England Nuclear) was blown to dryness under a stream of nitrogen at 50° C. To the resulting residue was added dichloromethane (1 mL) followed by oxalyl chloride (100 μL, 0.54 mmol). Vigorous gas evolution occurred for about 1.5 hr, at which point addition of additional oxalyl chloride (20 μL) did not produce any visible reaction. A 10% solution of dimethylformamide in dichloromethan (20 μL) was added which resulted in a change in color to greenish yellow. Addition of oxalyl chloride (20 μL, 0.761 mmol total) did not produce visible reaction and the reaction mixture was stirred at 0° C. for 12 hr. The mixture was allowed to warm to room temperature, diluted with dichloromethane (3 mL), counted (2.37 mCi), and washed with 5% sodium bicarbonate solution (2×1 mL) followed by 2% sodium bisulfite solution (1 mL). The dichloromethane solution was dried over sodium sulfate and stored in dry CH$_2$Cl$_2$ at −78° C. in a desiccator. HPLC: Zorbax SB-C8 4.8×250 mm analytical column, 80% water (containing 0.1% trifluoroacetic acid): 20% acetonitrile to 20% water(containing 0.1% trifluoroacetic acid): 80% acetonitrile in 30 min., UV=254 nm, Flow rate=1 ml/min, Retention time (Rt) of [$^{35}$S]-methanesulfonyl chloride=9.2 min. Measurement of the radioactivity by counting the resulting solution indicated 1.75 mCi (approx 58% yield) to be present. The details for the preparation of the [$^{35}$S]-methanesulfonyl chloride is described in "Development of a High Specific Activity Sulfur-35 Labelled Sulfonamide Radioligand That Allowed the Identification of a New Growth Hormone Secretagogue Receptor." Dean, D. C., Nargund, R. P., Melillo, D. G., Pong, S. S., Patchett, A. A., Smith, R. G, Chaung, L. P., Ellsworth, R. L., Griffin, P., Van der Ploeg, L. J. Med. Chem. 1996, 39, 1767.

Step C: Preparation of [$^{35}$S]-N-[1'-(6-cyano-1,2,3,4-tetrahydro-2(R)-naphthalenyl)-3,4-dihydro-4(R)-hydroxyspiro[2H-1-benzopyran-2,4'-piperidin]-6-yl] methanesulfonamide From a stock solution of [$^{35}$S]-methanesulfonyl chloride in CH$_2$Cl$_2$ (freshly dried over anhydrous sodium sulfate), 25 mCi of [$^{35}$S]-methanesulfonyl chloride was transferred into a 25 ml pear shaped flask and excess solvent was distilled at atmospheric pressure at 60–64° C. The distillation was stopped when the volume of solution was about 100–200 μl. The flask was removed from the heating bath and allowed to cool slightly. This solution was then transferred via blunt-end syringe to a solution containing amine product of Example 1, Step D (~5 mg, ~5000 fold excess relative to the [$^{35}$S]-methanesulfonyl chloride) in 30 μl of anhydrous CH$_2$Cl$_2$. The distillation flask was rinsed with anhydrous CH$_2$Cl$_2$ (2×50 μl) and combining organic solvent was transferred to the reaction mixture. To this solution, was added 10 μl of anhydrous triethylamine (stored under activated molecular sieves 4A). The reaction mixture was stirred at room temperature for 2 hr. The reaction mixture was assayed by HPLC analysis by quenching a aliquot of the reaction solution (<0.1 μL) into HPLC eluent (HPLC system: Zorbax-SB-C8 4.5×250 mm analytical column, 70% water (containing 0.1% HClO$_4$): 30% acetonitrile for 30 min to 100% MeCN over 10 min, then hold for 10 min, UV=230 nm, flow rate=1 ml /min, Rt of [$^{35}$S]MeSO$_3$H=3.1 min, Rt of amine 1=5.1 min, Rt of [$^{35}$S]sulfonamide was 10.1 min, ~50% [$^{35}$S]MeSO$_3$H, 45% radiochemical yield).

The reaction was diluted with 200 μl of water and 10 μl of trifluoroacetic acid (in order to deprotect the O-trimethylsilyl group). After stirring for 30 min at room temperature, the reaction mixture was diluted with 5 ml CH$_2$Cl$_2$ and stirred vigorously. The dichloromethane layer was separated and washed with saturated sodium bicarbonate (2×2 ml). The aqueous layer was extracted with CH$_2$Cl$_2$ (2×10 ml). The combined organic layer was dried over anhydrous sodium sulfate and evaporated to dryness using a rotary evaporator under reduced pressure. The resulting residue was dissolved in a mixture of acetonitrile:water (2:1 v:v) and purified using preparative HPLC (Zorbax-SB-C8 9.4×250 mm semi prep column, 75% water containing 0.1% HClO$_4$: 25% acetonitrile, UV=230 nm, flow rate=3 ml/min,. R$_T$ of MK-0499=14.9 min.). The product-containing fractions were combined and neutralized with saturated sodium bicarbonate. Acetonitrile was removed by concentration under nitrogen in a polypropylene container and the resulting solution was passed through a Sep-Pak (Waters, C-18) cartridge. The cartridge was washed with water (10 ml), followed elution of the product with methanol (2×5 ml). The methanol fraction was collected and determined to have a total activity of 11.5 mCi.

This batch showed a 1.3% radiochemical impurity at 2.3 min and 1.1% impurity at 6.7 min. Therefore, this batch was again repurified using Zorbax-SB phenyl semi prep column using same conditions as above, followed by Sep-Pak purification. The total activity obtained was 8.832 mCi with radiochemical purity >99%. The compound of Formula I has a specific activity of 1368 Ci/mmol.

EXAMPLE 3
[$^{35}$S] MK499 Binding to hERG K$^+$ Channel in HEK 293 Cell Membranes

| Step A: Materials | |
|---|---|
| A. Buffers: | |
| 1. Assay buffer (pH 7.4, room temp): | |
| KCl | 60 mM |
| NaCl | 71.5 mM |
| CaCl$_2$ x 2H$_2$O | 1 mM |
| MgCl$_2$ x 6H$_2$O | 2 mM |
| Hepes | 10 mM |
| 2. Wash buffer (pH 7.4 at 4° C.): | |
| NaCl | 131.5 mM |
| CaCl$_2$ × 2H$_2$O | 1 mM |
| MgCl$_2$ × 6H$_2$O | 2 mM |
| Hepes | 10 mM |

B. Membranes:

Human embryonic kidney cells constitutively expressing hERG are harvested, homogenized in Tris-EDTA buffer (containing 50 mM Tris and 1 mM EDTA (pH 7.4)) and centrifuged at 45,000×g for 20 min. at 4° C. The pellet is resuspended in Tris-EDTA buffer, re-homogenized and centrifuged as above. Finally, the pellet is resuspended in Tris-EDTA buffer, aliquoted and stored at −70° C. Membranes are briefly homogenized on the day of experiment and each aliquot is used only once.

C. Radioligand: Formula I at a Final Concentration of 50 pM
D. Non-specific Displacer: Formula II; 1 μM)
E. Cells: Cells are HEK 293 stably transfected with hERG cDNA. See Z. Zhou, et al. Biophysical Journal 74 pp. 230–241 (1998). They are in frozen medium. They should be cultured in minimum essential medium (MEM) supplemented with Earle's salts, nonessential amino acids (0.1 mM), sodium pyruvate (1 mM), penicillin (50 units/ml), streptomycin (50 μg/ml), geneticin (G418, Gibco BRL, 0.4 mg/ml) and fetal bovine serum (10%).

Step B: Binding Assay

Human ERG (hERG) membranes are diluted into assay buffer, mixed with radioligand to final concentration 50 pM and 400 μl of membrane/ligand mixture is added per well to 96 well assay blocks (Costar, Cat.#3957), containing 4 μl of 100×stocks of tested drugs or 100% DMSO (max. binding) or 100 μM solution of compound of Formula II (non-specific binding). The final membrane protein concentration in the assay is 11 μg/ml. This mixture is incubated at room temperature for 75 min., then filtered through GF/B Unifilters (Packard) presoaked in 0.1% BSA and washed 5×500 μl with ice-cold wash buffer. The filters are dried inside the fume hood at room temperature, 50 μl Microscint-20 is added to each well and Unifilters are counted for 1 min. in Topcount (Packard).

What is claimed is:

1. A method for characterizing the activity of a compound as an I$_{Kr}$ channel blocker comprising contacting the test compound with a membrane containing the I$_{Kr}$ channel, derived from a cell line transfected with the human ERG gene, in the presence of the radioligand compound

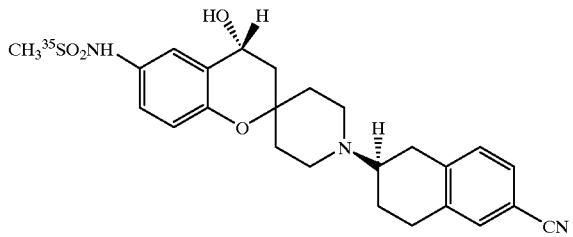

or a pharmaceutically acceptable salt thereof, monitoring whether the test compound influences the binding of the radioligand compound to the membrane containing the I$_{Kr}$ channel, and determining the I$_{Kr}$ channel blocker activity of the test compound.

2. The method as recited in claim 1, wherein the cell line in HEK 293 cells of CHO cells.

3. The method as recited in claim 2, wherein the radioligand compound of Formula I possesses a specific activity of in the range of about 900 Ci/mmol. to about 1498 Ci/mmol.

4. A method for assessing the binding of a test compound to a membrane containing the I$_{Kr}$ channel, derived from a cell line transfected with the human ERG gene, using a radioligand compound of Formula I, [$^{35}$S]-radiolabeled (+)-N-[1'-(6-cyano-1,2,3,4-tetrahydro-2(R)-naphthalenyl)-3,4-dihydro-4(R)-hydoxyspiro[2H-1-benzopyran-2,4'-piperidin]-6-yl]-methanesulfonamide, comprising the steps of:

1) preparing solutions of the test compound at about 5 or more different concentrations, a solution of control vehicle and a solution of (+)-N-[1'-(6-cyano-1,2,3,4-tetrahydro-2(R)-naphthalenyl)-3,4-dihydro-4(R)-hydoxyspiro[2H-1-benzopyran-2,4'-piperidin]-6-yl]-methansulfonamide (compound of Formula II) in a solvent;

2) mixing the radioligand compound of Formula I with the membrane containing the I$_{Kr}$ channel diluted with an assay buffer to form a membrane/radioligand mixture of known concentration;

3) incubating a quantity of the membrane/radioligand mixture with the solution of test compound, control vehicle or compound of Formula II, as recited in Step 1, for a set time period at a temperature range of between about 4° C. and about 37° C. to give a mixture of membrane bound with the radioligand and the test compound, the control vehicle or the compound of Formula II;

4) isolating from the incubated mixture the membrane bound with the radioligand and the test compound, the membrane bound with the radioligand and with the control vehicle or the membrane bound with the radioligand and the compound of Formula II;

5) measuring the radioactivity of the isolated membrane bound with the radioligand and the test compound, the membrane bound with the radioligand and with the control vehicle or the membrane bound with the radioligand and the compound of Formula II;

6) repeating steps 3 through 5 with the test compound at each concentration, the solution of control vehicle and the solution of the compound of Formula II, as recited in Step 1;

7) calculating the $IC_{50}$ corresponding to the measured radioactivity of: 1) the membrane bound with the radioligand and each concentration of the test compound; 2) the membrane bound with the radioligand and with the control vehicle, and 3) the membrane bound with the radioligand and the compound of Formula II, to access the binding of the test compound to the membrane.

5. The method as recited in claim 4, wherein the cell line in HEK 293 cells of CHO cells.

6. The method as recited in claim 5, wherein the solutions of the test compound are prepared in Step 1 at 7 different concentrations.

7. The method as recited in claim 6, wherein the time period for incubation in Step 3, is about 30 minutes to 1 hour.

8. The method as recited in claim 7, wherein the temperature for the incubation in Step 3, is room temperature (25° C.).

9. The method as recited in claim 8, wherein the membrane-bound with radioligand or test compound is isolated in Step 4 with Unifilters, Scintillation Proximity Assay (SPA) beads or the Flashplates.

10. The method as recited in claim 9, wherein the membrane containing the $I_{Kr}$ channel is derived from HEK 293 cell line transfected with the human ERG gene.

11. The method as recited in claim 10, wherein the radioligand compound of Formula I possesses a specific activity of in the range of about 900 Ci/mmol. to about 1498 Ci/mmol.

12. A method for assessing the binding of a test compound to a membrane containing the $I_{Kr}$ channel derived from a cell line transfected with the human ERG gene, using a radioligand of Formula I, [$^{35}$S]-radiolabeled (+)-N-[1'-(6-cyano-1,2,3,4-tetrahydro-2(R)-naphthalenyl)-3,4-dihydro-4(R)-hydoxyspiro[2H-1-benzopyran-2,4'-piperidin]-6-yl]-methansulfonamide, comprising the steps of:

1) preparing assay wells with 4 μl of the test compound in dimethylsulfoxide (DMSO) diluted 100× assay buffer at 5 or more different concentrations, a control vehicle of DMSO and a DMSO solution of (+)-N-[1'-(6-cyano-1,2,3,4-tetrahydro-2(R)-naphthalenyl)-3,4-dihydro-4(R)-hydoxyspiro[2H-1-benzopyran-2,4'-piperidin]-6-yl]-methanesulfonamide (compound of Formula II);

2) adding the radioligand compound of Formula I at 50 pM to the membrane containing the $I_{Kr}$ channel diluted with the assay buffer to form a membrane/radioligand mixture;

3) incubating each assay well with 400 μl of the 50 pM membrane/radioligand mixture for about 75 minutes to about 90 minutes at room temperature (25° C.) to give assay wells containing the membrane bound with the radioligand and the test compound at each concentration, the DMSO control vehicle or the compound of Formula II where the final concentration of the membrane containing the $I_{Kr}$ channel is 11 μg/ml;

4) filtering the incubated assay wells through 0.1% BSA presoaked filters to isolate on the filters the membrane bound with the radioligand and the test compound at each concentration, the DMSO control vehicle or the compound of Formula II;

5) washing each of the filters containing the membrane bound with the radioligand and the test compound at each concentration, the DMSO control vehicle or the compound of Formula II about 5 times with 500 μl of ice cold wash buffer;

6) drying the washed-filters containing the membrane bound with the radioligand and the test compound at each concentration, the DMSO control vehicle or the compound of Formula II at room temperature in a fume hood;

7) adding 50 Tl Microscint-20 microscintillate to the dried-filters containing the membrane bound with the radioligand and the test compound at each concentration, the DMSO control vehicle or the compound of Formula II;

8) measuring the microscintillation count of the microscintillation-treated filters containing the membrane bound with the radioligand and the test compound at each concentration, the DMSO control vehicle or the compound of Formula II for one minute; and 9) calculating the $IC_{50}$ corresponding to the measured microscintillation count of: 1) the microscintillation-treated filters containing the membrane bound with the radioligand and each concentration of the test compoun, 2) the microscintilation-treated filters containing the membrane bound with the radioligand and with the control vehicle, and 3) the microscintillation-treated filters containing the membrane bound with the radioligand and the compound of Formula II.

13. The method as recited in claim 12, wherein the cell line in HEK 293 cells.

14. The method as recited in claim 13, wherein the solutions of the test compound are prepared in Step 1 at 7 different concentrations.

15. The method as recited in claim 14, wherein the radioligand compound of Formula I possesses a specific activity of in the range of about 900 Ci/mmol. to about 1498 Ci/mmol.

16. The method as recited in claim 15, wherein the membrane-bound with radioligand or test compound is filtered in Step 4 with the Unifilters.

* * * * *